United States Patent [19]

Mahood et al.

[11] Patent Number: 5,451,623
[45] Date of Patent: Sep. 19, 1995

[54] NEOALKYL ALKYLIDENE-2,2'-BISPHENYL AND BIPHENYL PHOSPHITE ESTERS

[75] Inventors: James A. Mahood, Parkersburg, W. Va.; Carloss L. Gray, Belpre, Ohio

[73] Assignee: General Electric Company, Pittsfield, Mass.

[21] Appl. No.: 292,161

[22] Filed: Aug. 17, 1994

Related U.S. Application Data

[63] Continuation of Ser. No. 96,105, Jul. 22, 1993, abandoned.

[51] Int. Cl.$^6$ .............................................. C08K 5/527
[52] U.S. Cl. ........................................ 524/117; 558/85
[58] Field of Search ............................ 558/85; 524/117

[56] References Cited

U.S. PATENT DOCUMENTS

| | | |
|---|---|---|
| 3,201,437 | 8/1965 | Friedman . |
| 4,288,391 | 9/1981 | Spivack . |
| 4,318,845 | 3/1982 | Spivack et al. .................... 524/117 |
| 4,351,759 | 9/1982 | Spivack ................................. 524/91 |
| 4,885,326 | 12/1989 | Haruna et al. ...................... 524/291 |

FOREIGN PATENT DOCUMENTS

| | | |
|---|---|---|
| 0336606 | 10/1989 | European Pat. Off. . |
| 2087399 | 5/1982 | United Kingdom . |
| WO85/03702 | 8/1985 | WIPO . |

OTHER PUBLICATIONS

Paul A. Odorisio, Stpehen D. Pastor, John D. Spivack and Leander Steinhuebel, "12H–Dibenzo[d,g][1,3,2]Diosaphosphocins: Synthesis and Evidence for Long-Range Coupling to Phosphorus," *Phosphorus and Sulfur,* 1983, vol. 15, pp. 9–13.

*Primary Examiner*—Veronica P. Hoke

[57] ABSTRACT

Neoalkyl alkylidene-2,2'-bisphenyl phosphite esters are provided. The phosphites exhibit enhanced thermal and hydrolytic stability, and are useful as additives in thermoplastic resin compositions to enhance the thermal oxidative stability thereof.

9 Claims, No Drawings

NEOALKYL ALKYLIDENE-2,2'-BISPHENYL AND BIPHENYL PHOSPHITE ESTERS

This is a continuation of application Ser. No. 08/096,105 filed on Jul. 22, 1993 now abandoned.

BACKGROUND OF THE INVENTION

1. Field of the Invention

The present invention relates to phosphites, and more particularly relates to cyclic bisphenyl phosphites and thermoplastic resin compositions stabilized therewith.

2. Description of the Related Art

Cyclic biphenyl and bisphenyl monophosphites and their use as stabilizers in thermoplastic compositions are known, see Haruna U.S. Pat. No. 4,885,326 and Spivack U.S. Pat. No. 4,351,759, both of which are incorporated herein by reference. Many of these cyclic bisphenyl and biphenyl monophosphites experience less than desirable levels of thermal and/or hydrolytic stability.

Consequently, there is a need to provide cyclic bisphenyl and biphenyl phosphites that exhibit enhanced levels of thermal and/or hydrolytic stability.

SUMMARY OF THE INVENTION

Neo alkyl alkylidene-2,2'-bisphenyl and biphenyl phosphite esters are provided. The phosphites may be represented by the general formula:

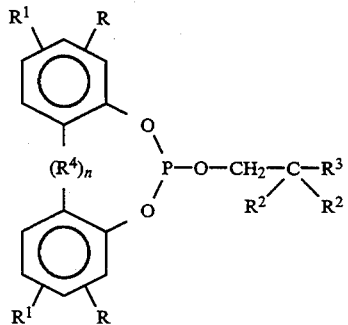

wherein each R is independently selected from the group consisting of alkyls having from 1 to 18 carbon atoms, each $R^1$ is independently selected from the group consisting of hydrogen and alkyls having from 1 to 18 carbon atoms, each $R^2$ is independently selected from the group consisting of alkyls having from 1 to 18 carbon atoms, and $R^3$ is selected from the group consisting of alkyls having from 1 to 30 carbon atoms, alkylethers having from 1 to 30 carbon atoms and an aliphatic carboxylic acid ester having from 1 to 30 carbon atoms, and $R^4$ is selected from the group consisting of alkylenes having from 1 to 12 carbon atoms and arylenes having from 1 to 12 carbon atoms, and n is 0 or 1. When n=1, $R^4$ is such that no more than one carbon atom separates the aryl groups connected by $R^4$, and when n=0, a carbon to carbon direct bond connects the two aryl groups. The phosphites are useful as additives in thermoplastic compositions to improve the thermal oxidative stability thereof.

DETAILED DESCRIPTION OF THE INVENTION

The compounds of the present invention may be represented by the general formula:

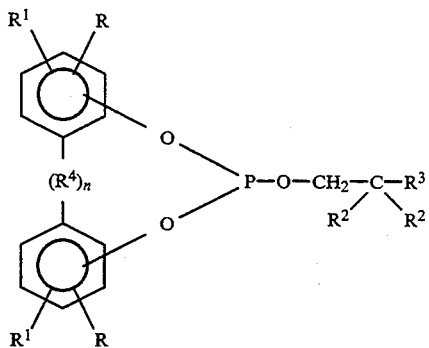

wherein each R is independently selected from the group consisting of alkyls having from 1 to 18 carbon atoms, each $R^1$ is independently selected from the group consisting of hydrogen and alkyls having from 1 to 18 carbon atoms, preferably each $R^2$ is independently selected from the group consisting of alkyls having from 1 to 30 carbon atoms, and $R^3$ is selected from the group consisting of alkyls having from 1 to 18 carbon atoms, alkylethers having from 1 to 18 carbon atoms, alkyls having from 1 to 30 carbon atoms and an aliphatic carboxylic acid ester having from 1 to 18 carbon atoms, and $R^4$ is selected from the group consisting of alkylenes having from 1 to 12 carbon atoms and arylenes having from 1 to 12 carbon atoms, and n is 0 or 1. Wherein R is preferably straight-chain or branched alkyl with 1-8 carbon atoms, such as methyl, ethyl, n-propyl, iso-propyl, n-butyl, sec-butyl, tert-butyl, 2-ethylhexyl and n-octyl and tert-octyl, and α-branched alkyl radicals with 3-8 carbon atoms are more preferred. The R groups tert-butyl and tert-octyl are especially preferred. Preferably R is in the ortho position to the oxygen. Also especially preferred is for the $R^1$ group to be in the para position to oxygen, particularly if $R^1$ is tert-alkyl.

The phosphites may also be represented by the formulas

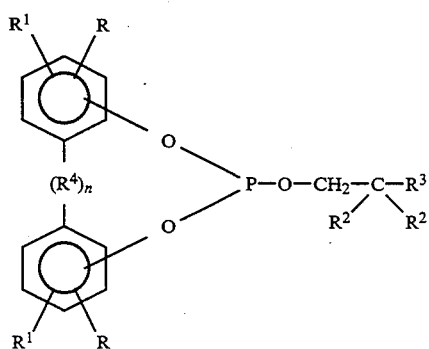

-continued

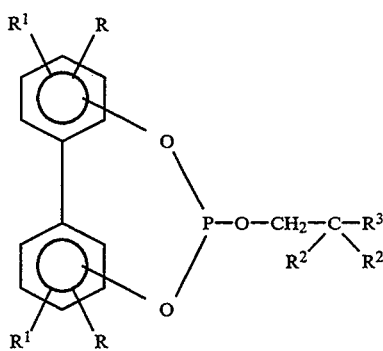

Although R¹ can be hydrogen or alkyl of 1 to 18 carbons, preferably it is an alkyl group of 1 to 8 carbon atoms, either straight-chain or branched-chain. Especially preferred is tert-alkyl of 4 to 8 carbon atoms, and more preferably tert butyl.

Each $R^2$ is preferably independently an alkyl group having from 1 to 30 carbon atoms, including for example, methyl, ethyl, propyl, isopropyl, butyl, secondary butyl, tertiary butyl, isobutyl, amyl, tertiary amyl, hexyl, heptyl, octyl, isooctyl, 2-ethylhexyl, tertiary octyl, nonyl, tertiary nonyl, decyl, isodecyl, dodecyl, tetradecyl, hexadecyl, octadecyl, docosyl, tetracosyl, tracontyl and so forth. Although less preferred, and most likely less stable, some stability can be exhibited where one $R^2$ is hydrogen and the other $R^2$ is an alkyl.

$R^3$ is preferably an alkyl group of 1 to 18 carbon atoms, phenyl, or phenyl substituted with up to 3 alkyl groups each having 1 to 8 carbon atoms. The group $R^3$ can be alkyl of 1 to 18 carbon atoms, such as methyl, ethyl, butyl, hexyl, heptyl, octyl, decyl, dodecyl, octadecyl and the like; or it can be phenyl or alkyl substituted phenyl, such as tolyl, xylyl, mesitylyl, ethylphenyl, butyl-phenyl, 3,5-dibutylphenyl, p-octylphenyl, 3,5-dioctylphenyl and the like. Preferably $R^3$ is a phenyl group having at least one branched alkyl group. Most preferably $R^3$ is 2-tert-butylphenyl, 2,4-di-tert-butylphenyl, 2,4,6-tri-tert butylphenyl, 2-tert-butyl-5-methylphenyl, 2,6-di-tert-butyl-phenyl and 2,6-di-tert-butyl-4-methyl-phenyl, 2,4-di-tert-octylphenyl. Preferably $R^4$ is alkylene having from 1 to 12 carbon atoms or arylene having from 1 to 12 carbon atoms.

$R^4$ is preferably alkylene or arylene of the formula:

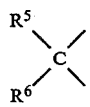

wherein $R^5$ and $R^6$ are independently hydrogen, alkyl or aryl radicals. Typical arylene groups for purposes of these various $R^4$ include phenylene, tolylene, mesitylene, xylylene and 1- and 2-naphthylene, Especially preferred as $R^4$ is methylene or ethylidene, n is preferably 1. Suitable phosphites are set out below:

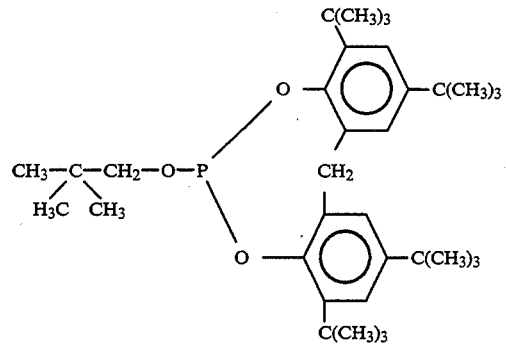

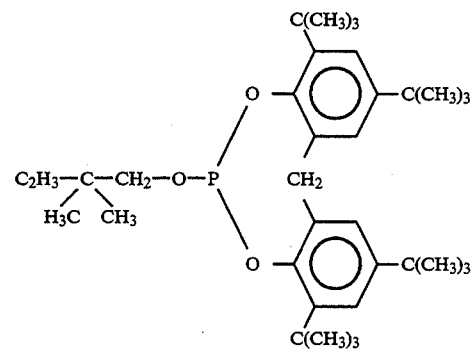

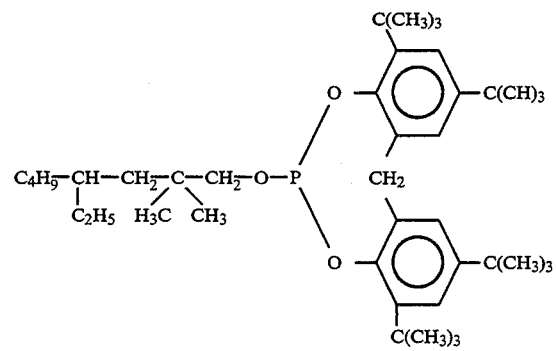

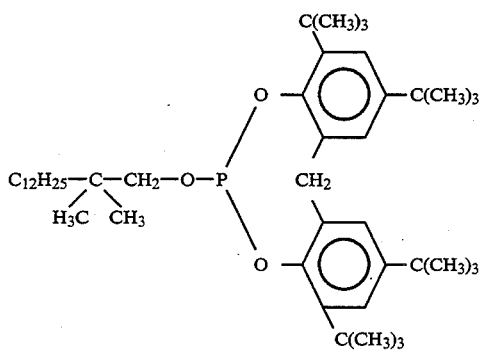

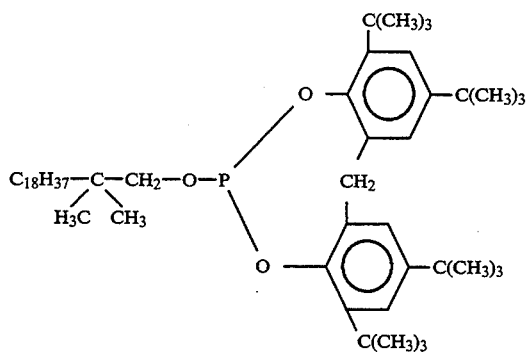

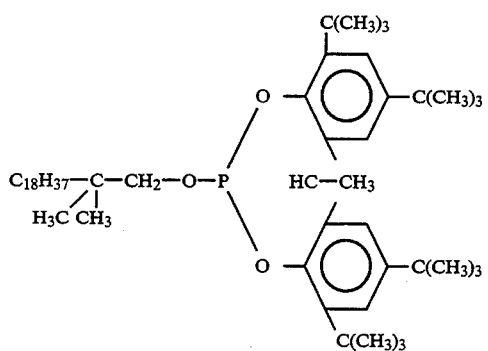

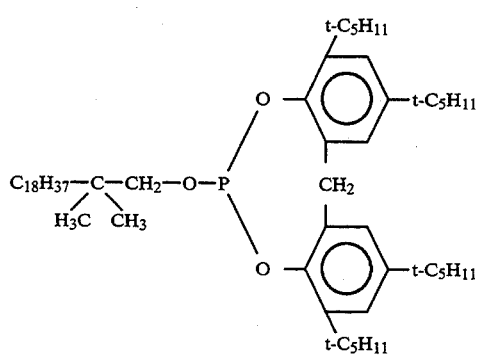

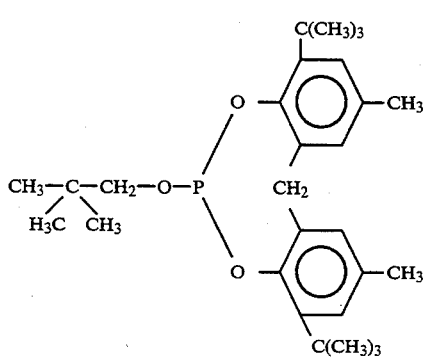

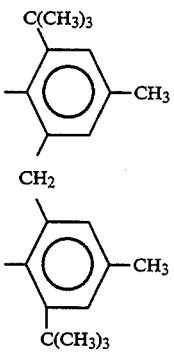

The compound can be obtained by allowing, for example, phosphorous trichloride to react with 2,2'-alkylidenebisphenol into a compound which will then be allowed to react with an alcohol represented by $$R^3-\underset{R^2}{\underset{|}{C}}-CH_2-OH.$$

$R^3$ is preferably selected from the group consisting of:

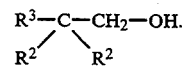

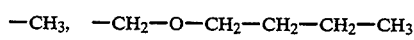

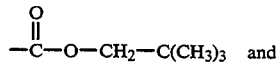

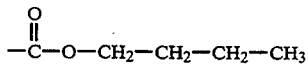

Each $R^2$ is preferably a methyl group.

Thermoplastic compositions containing a polymer and an amount of the present phosphite can be made by blending. The phosphites of this invention are effective antioxidants which may be employed in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene, with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methylacrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from $\alpha,\beta$-unsaturated acids and derivatives thereof, polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polyisobutylene oxide.
13. Polyphenylene oxides.
14. Polyurethanes and polyureas.
15. Polycarbonates.
16. Polysulphones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.
18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
19. Crosslinked polymers which are derived from aldehydes on the one hand and from phenols, ureas and melamines on the other, for example phenol/-formaldehyde, urea/formaldehyde and melamine/-formaldehyde resins.
20. Alkyd resins, for example glycerol/phthalic acid resins and mixtures thereof with melamine/formaldehyde resins.
21. Unsaturated polyester resins which are derived from copolyesters of saturated and unsaturated dicarboxylic acids with polyhydric alcohols as well as from vinyl compounds as crosslinking agents and also the halogen-containing, flame-resistant modifications thereof.
22. Natural polymers, for example cellulose, rubber, as well as the chemically modified homologous derivatives thereof, for example cellulose acetates, cellulose propionates and cellulose butyrates and the cellulose ethers, for example methyl cellulose.

The phosphites of this invention are particularly effective in stabilizing organic materials such as thermoplastic polymers, in addition to mineral and synthetic fluids such as lubricating oils, circulating oils, etc.

The phosphites of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methylpentene-1), various ethylene-propylene copolymers and the like.

Other polymers in which the phosphites of this invention are particularly useful are polystyrene, including impact polystyrene, ABS resin, SBR, isoprene, as well as natural rubber, polyesters including polyethylene terephthalate and polybutylene terephthalate, including copolymers. Other suitable polymers include polyurethanes, polycarbonates, polyamides such as nylon 6, 6/6 and the like as well as copolyamides and polysulfones.

The phosphites may be used with primary stabilizers such as phenolic antioxidants, a neutralizer such as calcium stearate, pigments, colorants or dyes, UV absorbers, light stabilizers such as hindered amines, metal deactivators, talc and other fillers, etc. Preferably the phosphites should be used in polymeric compositions in combination with a phenolic antioxidant and a neutralizer.

In general, the phosphites of this invention are employed at from about 0.01 to about 5% by weight based on the total weight of the stabilized thermoplastic composition, although this will vary with the particular polymer and application. An advantageous range is from about 0.05 to about 2% by weight thereof, and especially 0.1 to 1% by weight thereof.

The phosphites of this invention are useful to stabilize polymers especially during high temperature processing with relatively little change in color, even though the polymer may undergo a number of extrusions. Among the polymers in which this property is especially important are polypropylene, polyethylene, styrenics such as ABS, polyethylene- and polybutylene-terephthalates, polycarbonates, natural rubber, synthetic rubber such as SBR. These phosphites can be used as process stabilizers for polyolefins in the presence of costabilizers such as phenolic antioxidants. A particularly important property for stabilizers which are trivalent phosphorous esters is resistance to hydrolysis in the presence of moisture in the atmosphere during ambient storage. Thermal stability may be tested by evaluating color change of neat phosphite upon exposure to heat in the presence of air. Hydrolysis of phosphorous esters during storage frequently results in compounds which are less effective. The phosphites of the present invention exhibit both hydrolytic stability and thermal stability.

The phosphites of the present invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:
1. Antioxidants
   1.1 Simple 2,6-dialkylphenols, such as, for example, 2,6-di-tert.-butyl-4-methylphenol, 2-tert-butyl- 4,6-dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amylhydroquinone, 2,6-di-tert.-butylhydroquinone, 2,5-di-tert.-butyl-4-hydroxyanisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulphide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-(4-methyl-6(α-methylcyclohexyl)-phenol), 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-(3,3-bis-(3'-tert.butyl-4'-hydroxyphenyl)-butyrate).

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonate, such as, for example, dioctadecyl 2,2-bis-(3,5-di-tert.-butyl-2-hydroxybenzyl)-malonates, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-(4-(1,1,3,3-tetramethylbutyl)-phenyl) 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-(bis-B-(3,5-di-t-butyl-4-hydroxyphenyl)propionyl)-hydrazine.

1.10 Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonmediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicylo-(2,2,2)octane.

1.11 Esters of β-(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thio-pentadecanol, trimethylhexanediol trimethylolethane, trimethylolpropane, tris-hydroxyethyl isocyanurate and 4-hydroxymethyl-1-phospha-2,6,7-trioxabicyclo(2,2,2)octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo(2,2,2)-octane, especially the tetra-bis ester of pentaerythritol.

1.13 Benzylphosphonates, such as, for example, dimethyl 3,5-di-tert.-butyl-4-hydroxybenzylphosphonate, diethyl-3,5-di-tert.-butyl-4-hydroxybenzylphosphonate dioctadecyl 3,5-di-tert.butyl-4-hydroxybenzylphosphonate and di-octadecyl 5-tert.-butyl-4-hydroxy-3-methylbenzylphosphonate.

The following may be mentioned as examples of further additives that can be used together with the phosphite stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono and dioctyliminodibenzyl, polymerized 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sect-octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, di-phenylamineacetone condensation product, aldol-1-naphthylamine and phenothiazine.

2. UV-Absorbers and light-stabilizing agents
   2.1 2-(2'-Hydroxyphenyl)-benzotriazoles, e.g. the 5'-methyl-, 3',5'-di-tert.-butyl-, 5'-tert.-butyl-, 5'-(1,1,3,3-tetramethylbutyl)-, 5-chloro-3',5-di-tert. -butyl-, 5-chloro-3'-tert.-butyl-5'-methyl, 3'-sec.-butyl'5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3,5'-di-tert.-amyl-, 3'-methyl-5'-carbomethoxyethyl- and 5-chloro-3',5'-di-tert.-amyl-derivative.
   2.2 2,4-bis-(2'-Hydroxyphenyl)-6-alkyl-s-triazines, e.g. the 6-ethyl-, 6-heptadecyl- or 6-undecyl-derivative.
   2.3 2-Hydroxybenzophenones, e.g. the 4-hydroxy-, 4-methoxy-, 4-oxtoxy-, 4-decyloxy-, 4-dodecyloxy-, 4-benzyloxy-, 4,2',4'-trihydroxy- or 2'-hydroxy-4,4'-dimethoxy-derivative.
   2.4 1,3-bis-(2'-Hydroxybenzoyl)-benzenes, e.g. 1,3-bis-(2'-hydroxy-4'-hexyloxybenzoyl)-benzene, 1,3-bis-(2'-hydroxy-4'dodecyloxy-benzoyl)benzene.
   2.5 Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.
   2.6 Acrylates, e.g. α-cyano-β,β-diphenylacrylic acid-ethyl ester or isooctyl ester, α-carbomethoxy cinnamic acid methyl ester, α-cyano β-methyl-p-methoxycinnamic acid methyl ester or -butyl ester or N-(β-carbomethoxyvinyl)-2-methylindoline.
   2.7 Sterically hindered amines, e.g. 4-benzoyl-2,2,6,6-tetramethylpiperidine, 4-stearyloxy-2,2,6,6-tetramethylpiperidine, bis-( 2,2,6,6-tetramethylpiperidyl)sebacate or 3-n-octyl-7,7,9,9-tetramethyl-1,3,8-triazaspiro(4,5)decane-2,4-dione.
   2.8 Oxalic acid diamides, e.g. 4,4'-di-octyloxy-oxanilide, 2,2'-di-octyloxy-5,5'-di-tert.-butyl-oxanolide. 2.2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and paramethoxy- as well as of o- and p-ethoxy-disubstituted oxanilides.
3. Metal deactivators, e.g. oxanilide, isophthalic acid dihyrazide, sebacic acid-bis-phenylhydrazide, bis-benzylidene-oxalic acid dihydrazide, N,N'-diacetal-adipic acid dihydrazide, N,N'-bis-salicyloyloxalic acid dihydrazide, N,N'-bis-salicyloylhydrazine, N,N'-bis(3,5-di-tert.-butyl-4-hydroxyphenylpropionyl)hydrazine, N-salicyloyl-N'-salicylalhydrazine, 3-salicyloylamino-1,2,4-triazole or N,N'-bis-salicyloyl-thiopropionic acid dihydrazide.
4. Basic co-stabilizers, e.g. alkali metal salts and alkaline-earth metal salts of higher fatty acids, for example Ca-stearate, Zn-stearate, Mg-behenate, Na-ricinoleate or K-palmitate.
5. Nucleation agents, e.g. 4-tert.-butylbenzoic acid, adipic acid or diphenylacetic acid.
6. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa 3,9-diphospha(5,5)-undecane and tri-(4-hydroxy-3,5-di-tert.butyl-phenyl) phosphite.

Other additives that can be incorporated in the stabilized compositions are optionally thiosynergists such as dilauryl-thiodiproprionate or distearylthiodipropionate, lubricants such as stearyl alcohol fillers, carbon black, asbestos, lanolin, talc, glass fibers, pigments, optical brighteners, fireproofing agents and antistatic agents.

Polymeric particles may be coated with the present phosphites alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins, issued Nov. 24, 1987, both of which are disclosed herein by reference. Particle formation may be achieved by support Ziegler-Natta Catalyst systems. Suitable commercial processes are known by the trademarks: Spheripol, Addipol and Spherilene.

Olefin polymers may be produced by polymerization of olefins in the presence of Ziegler Natta catalysts optionally on supports such as but not limited to Mg $Cl_2$, chromium salts and complexes thereof, optionally supported on Silica or other materials. They may also be produced utilizing catalysts based on a cyclopentadiene complexes of metals typically complexes of Ti and Zr.

The following examples are meant to illustrate the present invention and not limit the scope thereof. The key advantage of the present materials are their combined hydrolytic and thermal stabilities.

EXAMPLES

EXAMPLE 1

A phosphite compound (PS) of the following formula:

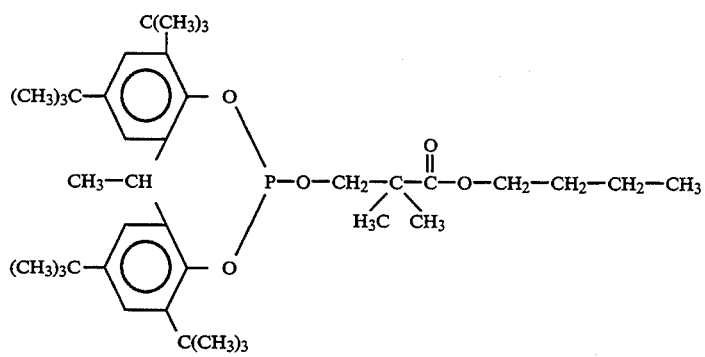

was prepared by the following procedure: a compound of the formula

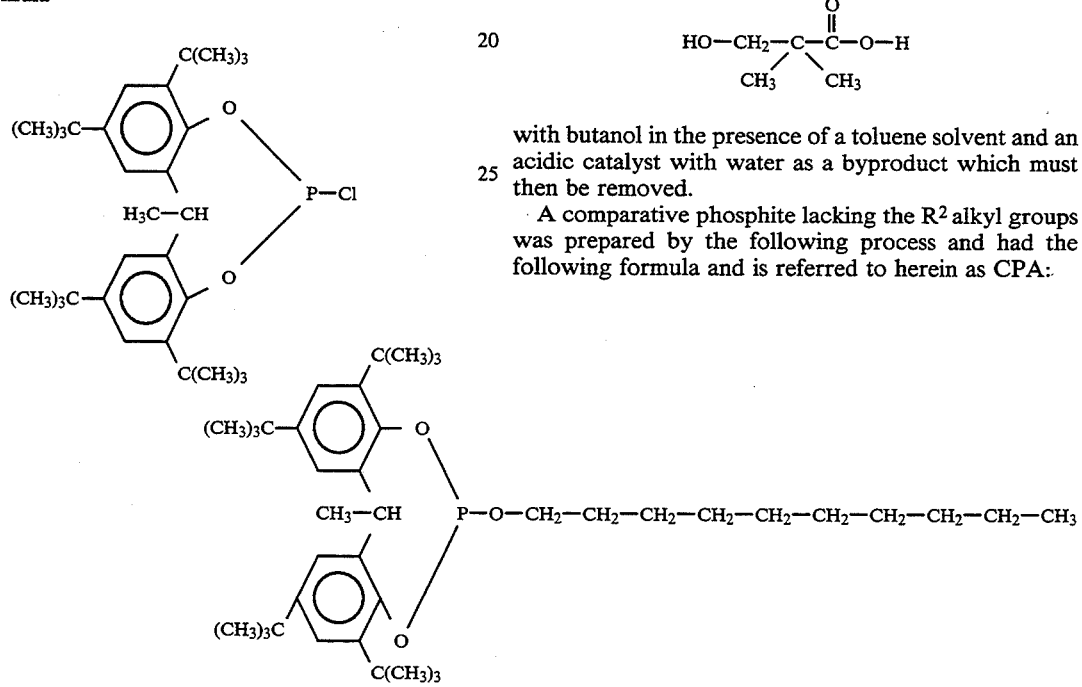

was reacted with

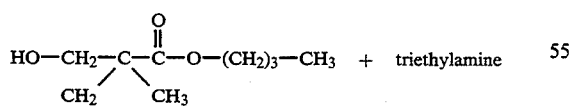

at room temperature, with presence of a hydrocarbon solvent such as heptane to yield the desired product plus a salt byproduct. The compound

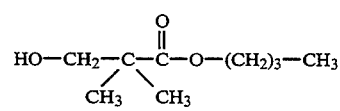

can be obtained by reacting

HO—CH$_2$—C(CH$_3$)(CH$_3$)—C(=O)—O—H with butanol in the presence of a toluene solvent and an acidic catalyst with water as a byproduct which must then be removed.

A comparative phosphite lacking the R$^2$ alkyl groups was prepared by the following process and had the following formula and is referred to herein as CPA:

TABLE 1

| Phosphite | Hours to 1% Weight GAIN |
|---|---|
| P2 | 2000+ |
| CPB | 120 |
| CPA | 200 |
| P3 | 2000+ |
| P4 | 2000+ |
| P5 | 2000+ |
| CPC | 2000+ |

P2 is a phosphite of the present invention and has the formula:

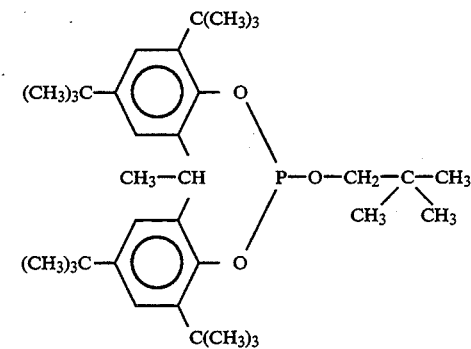
CPB is a comparative phosphite of the formula:
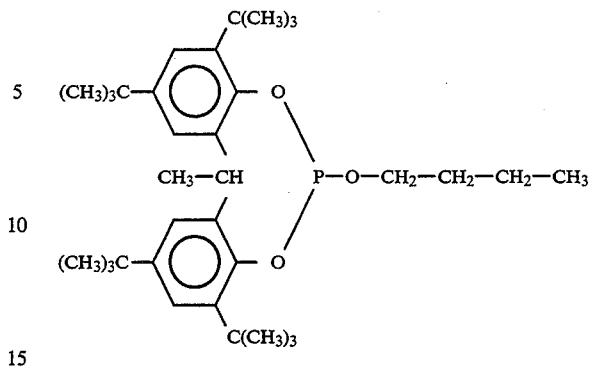
P3 is a phosphite of the present invention and has the formula:
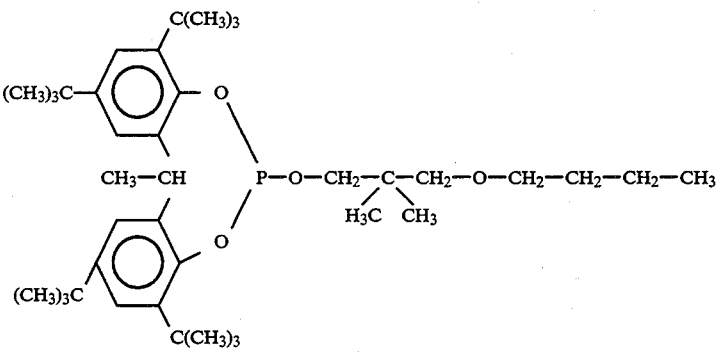
P4 is a phosphite of the present invention and has the following formula:
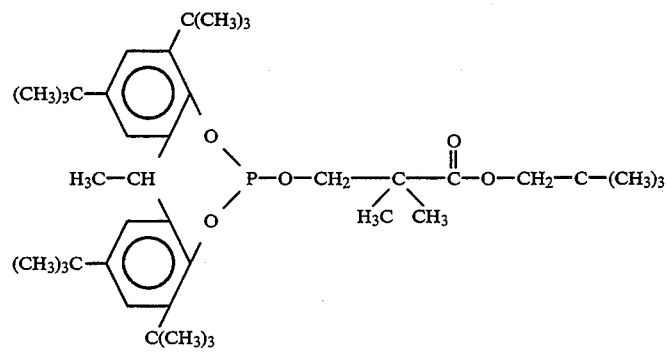
P5 is a phosphite of the present invention and has the formula:
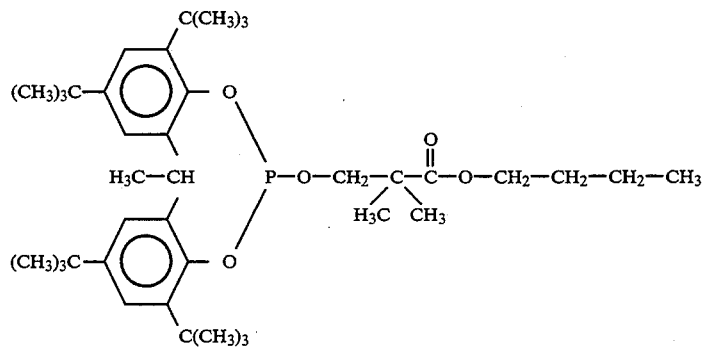
CPC is a phosphite of the formula:

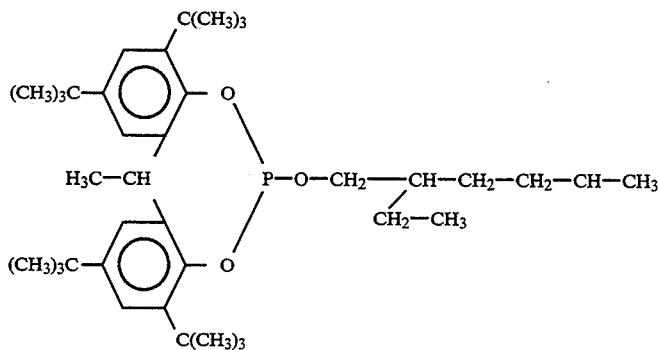

Note that the phosphites of the present invention had R² alkyl groups and exhibited enhanced hydrolytic stability.

As shown in Table 2, the phosphites of example 1 and comparative example A (CPC) were heated in air to 290° C. for 60 minutes resulting in the phosphite of example 1 remaining a clear slightly yellow liquid and the phosphite comparative example CPC changing from a clear yellow liquid to a transparent brown liquid with some formation of black material. The CPC phosphite exhibited good hydrolytic stability, but the one R² group being hydrogen, lacked the thermal stability of the phosphites of the present invention.

TABLE 2

| | | Color Change Upon Exposure to Heat | |
|---|---|---|---|
| Ex | Phos | Neat Phosphate | Polypropylene Compound |
| A | CPC | Light Brown Color Formed | formation of some dark material in the mass |
| 1 | P5 | Slight yellowing | slight yellowing in the mass |

The darkening of the CPC material is undesirable because it indicates that the CPC material is degrading upon exposure to heat in presence of air. The CPC material when added to polymer such as polypropylene and pressed at elevated temperatures (for example 290° C.) in the presence of air will tend to generate undesired dark material which in turn can form such material as char and/or black specks. The addition of P5 to polypropylene and processing thereto at elevated temperature (290° C.) result in only slight yellowing of the polymeric mass.

We claim:

1. A thermoplastic resin composition comprising:
   (a) a polyolefin resin; and
   (b) a phosphite, which is present in a thermal stabilizing amount and which is selected from the group of phosphites of the formulae:

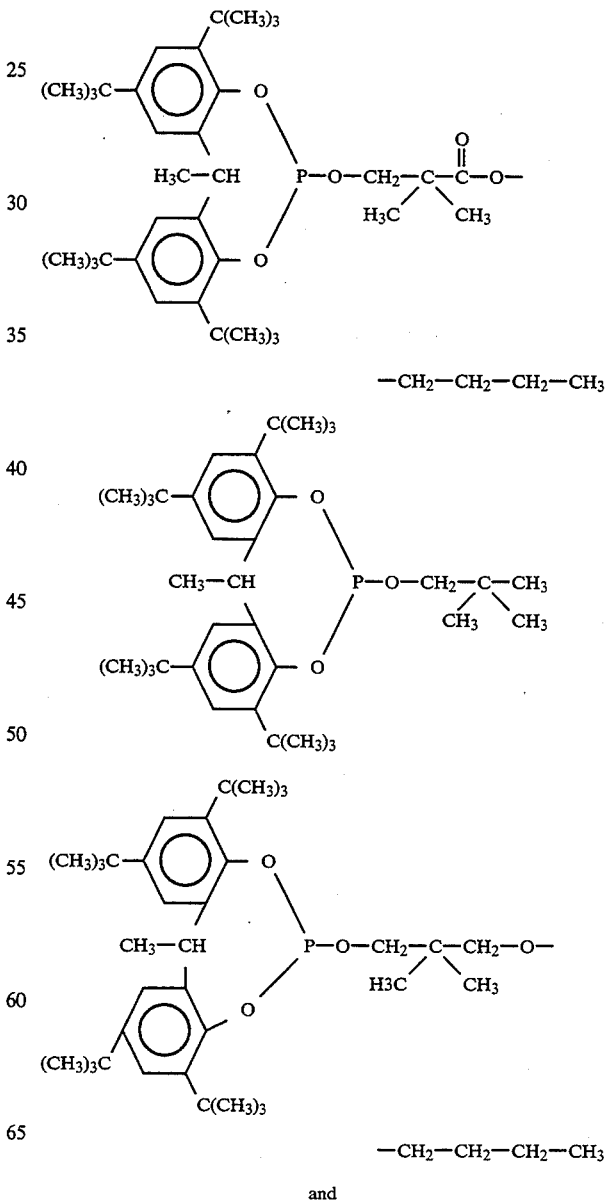

and

5. The composition of claim 1 wherein said phosphite is present at a level of from 0.1 to 1 percent by weight based on the total weight of the composition.

6. The composition of claim 1 wherein said phosphite is of the formula:

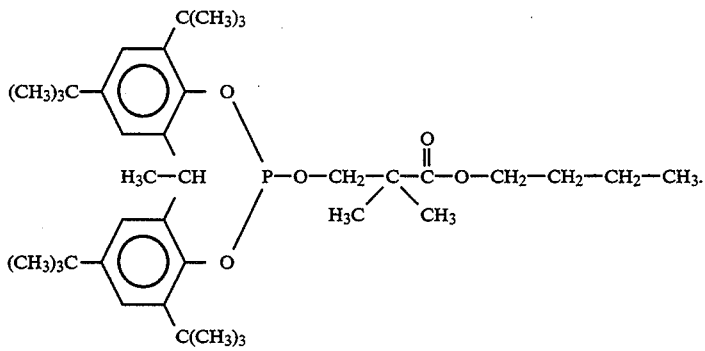

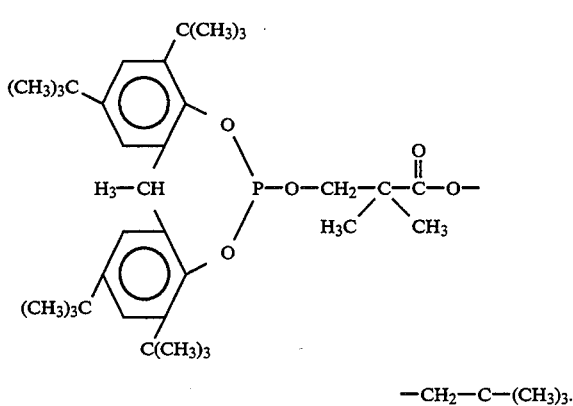

—CH₂—C—(CH₃)₃.

2. The composition of claim 1 wherein said polyolefin resin is polypropylene resin.

3. The composition of claim 1 wherein said phosphite is present at a level of from 0.01 to 5 percent by weight based on the total weight of the composition.

4. The composition of claim 1 wherein said phosphite is present at a level of from 0.05 to 2 percent by weight based on the total weight of the composition.

7. The composition of claim 1 wherein said phosphite is of the formula

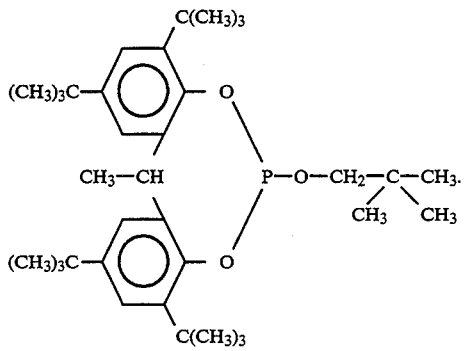

8. The composition of claim 1 wherein said phosphite is of the formula

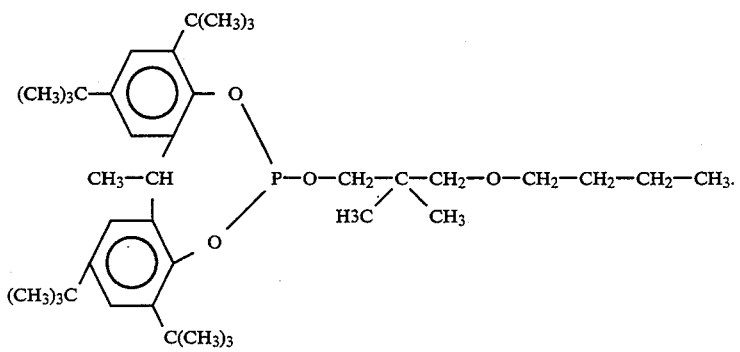

9. The composition of claim 1 wherein said phosphite is represented by the formula

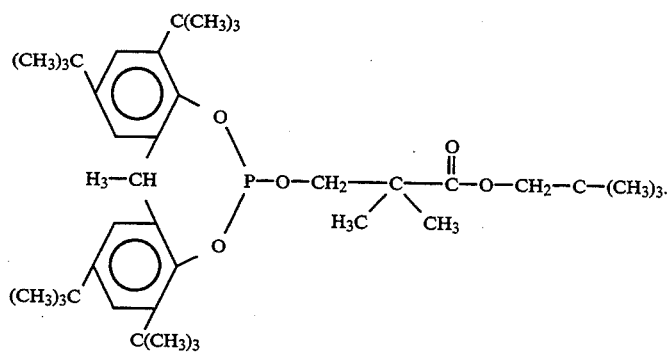
* * * * *